(12) United States Patent
Liaw et al.

(10) Patent No.: US 7,118,894 B2
(45) Date of Patent: Oct. 10, 2006

(54) BACTERIAL STRAINS, METHODS OF PREPARING THE SAME AND USE THEREOF IN FERMENTATION PROCESSES FOR L-LYSINE PRODUCTION

(75) Inventors: Hungming J Liaw, Champaign, IL (US); John Eddington, Decatur, IL (US); Yueqin Yang, Decatur, IL (US); Richard Dancey, Mt. Zion, IL (US); Stacia Swisher, Decatur, IL (US); Weiying Mao, Decatur, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 10/283,075

(22) Filed: Oct. 30, 2002

(65) Prior Publication Data
US 2003/0113878 A1 Jun. 19, 2003

Related U.S. Application Data

(62) Division of application No. 09/630,454, filed on Aug. 2, 2000, now Pat. No. 6,984,512.

(60) Provisional application No. 60/146,350, filed on Aug. 2, 1999.

(51) Int. Cl.
C12P 19/24 (2006.01)
C12P 1/04 (2006.01)
C12N 15/01 (2006.01)

(52) U.S. Cl. ............... 435/115; 435/170; 435/446

(58) Field of Classification Search ........ 435/106–116, 435/170, 446
See application file for complete search history.

(56) References Cited

U.S. PATENT DOCUMENTS

| 2,979,439 | A | 4/1961 | Kinoshita et al. ............ 435/115 |
| 3,687,810 | A | 8/1972 | Kurihara et al. ............. 435/115 |
| 3,700,557 | A | 10/1972 | Nakayama et al. .......... 435/115 |
| 3,707,441 | A | 12/1972 | Shiio et al. ................ 435/115 |
| 3,708,395 | A | 1/1973 | Nakayama et al. .......... 435/115 |
| 3,825,472 | A | 7/1974 | Kubota et al. .............. 435/115 |
| 4,169,763 | A | 10/1979 | Nakayama et al. .......... 435/115 |
| 4,560,654 | A | 12/1985 | Miwa et al. ................ 435/115 |
| 5,236,831 | A | 8/1993 | Katsumata et al. .......... 435/106 |
| 5,650,304 | A | 7/1997 | Ishii et al. ................ 435/115 |
| 5,766,925 | A | 6/1998 | Sugimoto et al. ....... 435/252.32 |
| 5,846,790 | A | 12/1998 | Kimura et al. ............. 435/110 |
| 5,939,307 | A | 8/1999 | Wang et al. ............ 435/252.33 |

OTHER PUBLICATIONS

Nakamori et al. 46: 487-491, 1982.*
Udeh et al. Acta Microbiologica Polonica 42: 171-180, 1993.*
Sonntag, K., et al., "Flux partitioning in the split pathway of lysine synthesis in *Corynebacterium glutamicum*," *Eur. J. Biochem.* 213:1325-1331, Blackwell Science Ltd. (1993).
Wehrmann, A., "Different Modes of Diaminopimelate Synthesis and Their Role in Cell Wall Integrity: a Study with *Corynebacterium glutamicum*," *J. Bacteriol.* 180:3159-3165, American Society for Microbiology (Jun. 1998).
International Search Report for International Patent Application No. PCT/US00/20899 mailed Mar. 6, 2001.
Kleemann, A., et al., " Amino Acids," in *Ullmann's Encyclopedia of Industrial Chemistry*, vol. A2, Gerhartz, W., et al., eds., Weinham: VCH-Verlagsgesellschaft, pp. 57-97 (1985).
Nakayama, K., et al., "Microbial Production of Essential Amino Acids with *Corynebacterium glutamicum* Mutants," in *Nutritional Improvement of Food and Feed Proteins*, M. Friedman, ed., pp. 649-661 (1978).
Sahm, H., et al., "Construction of L-Lysine- , L-Threonine- , or L-Isoleucine-Overproducing Strains of *Corynebacterium glutamicum*," *Ann. N.Y. Acad. Sci.* 782:25-39, Springer Press (1996).
Bröer, S., and Krämer, R., "Lysine Excretion by *Corynebacterium glutamicum*. 2. Energetics and Mechanism of the Transport System," *Eur. J. Biochem.* 202:137-143, Springer International (1991).
Hsiao T. -Y. and Glatz, C.E., "Water Reuse in the L-Lysine Fermentation Process," *Biotechnol. Bioengin.* 49:341-347, John Wiley & Sons, Inc. (1996).
Kinoshita, S., et al., "Glutamic Acid Fermentation," *Proc. Int. Symp. Enzyme Chem.* 2:464-468, Pan Pacific Press (1958).

* cited by examiner

*Primary Examiner*—S. Devi
(74) *Attorney, Agent, or Firm*—Buchanan Ingersoll & Rooney PC; Craig G. Cochenour; Duane A. Stewart, III

(57) ABSTRACT

The invention provides novel microorganisms, methods for the production thereof and novel processes for the production of amino acids. Mutagenesis of parental bacterial strains and selection of an improved raffinate-resistant phenotype enables the isolation of strains with enhanced growth properties that produce larger amounts of amino acid. Microorganisms of the invention are produced from amino acid producing parental strains such as *Corynebacterium* or *Brevibacterium*, particularly preferred are parental strains that produce L-lysine.

6 Claims, 2 Drawing Sheets

BACTERIAL STRAINS, METHODS OF PREPARING THE SAME AND USE THEREOF IN FERMENTATION PROCESSES FOR L-LYSINE PRODUCTION

This application is a divisional of U.S. application Ser. No. 09/630,454, filed Aug 2, 2000, now U.S. Pat. No. 6,984,512 which claims benefit to the filing date of U.S. Provisional application 60/146,350, filed Aug. 2, 1999 (now abandoned) each of which is incorporated by reference in its entirety.

BACKGROUND OF THE INVENTION

1. Field of the Invention

The present invention relates to the fields of microbiology and microbial genetics. More specifically, the invention relates to novel bacterial strains, methods and processes useful for the fermentative production of amino acids.

2. Related Art

Following the recognition that Corynebacteria were useful for the fermentative production of amino acids (S. Kinoshita et al., *Proceedings of the International Symposium on Enzyme Chemistry* 2:464–468 (1957)), the industrial production of L-lysine became an economically important industrial process. Commercial production of this essential amino acid is principally done utilizing the gram positive *Corynebacterium glutamicum*, *Brevibacterium flavum* and *Brevibacterium lactofermentum* (Kleemann, A., et. al., "Amino Acids," in ULLMANN'S ENCYCLOPEDIA OF INDUSTRIAL CHEMISTRY, vol. A2, pp.57–97, Weinham: VCH-Verlagsgesellschaft (1985)). These organisms presently account for the approximately 250,000 tons of L-lysine produced annually.

The efficiency of commercial production of L-lysine may be increased by the isolation of mutant bacterial strains which produce larger amounts of L-lysine. Microorganisms employed in microbial process for amino acid production are divided into 4 classes: wild-type strain, auxotrophic mutant. regulatory mutant and auxotrophic regulatory mutant (K. Nakayama et al., in *Nutritional Improvement of Food and Feed Proteins*, M. Friedman, ed., (1978), pp.649–661). Mutants of *Corynebacterium* and related organisms enable inexpensive production of amino acids from cheap carbon sources, e.g., mollasses, acetic acid and ethanol, by direct fermentation. In addition, the stereospecificity of the amino acids produced by fermentation (the L isomer) makes the process advantageous compared with synthetic processes.

Given the economic importance of L-lysine production by the fermentive process, the biochemical pathway for lysine synthesis has been intensively investigated, ostensibly for the purpose of increasing the total amount of L-lysine produced and decreasing production costs (recently reviewed by Sahm et al., *Ann. N. Y. Acad. Sci.* 782:25–39 (1996)). Entry into the lysine pathway begins with L-aspartate (see FIG. 1), which itself is produced by transamination of oxaloacetate. A special feature of *C. glutamicum* is its ability to convert the lysine intermediate piperidine 2,6-dicarboxylate to diaminopimelate by two different routes, i.e., by reactions involving succinylated intermediates or by the single reaction of diaminopimelate dehydrogenase. Overall, carbon flux into the pathway is regulated at two points: first, through feedback inhibition of aspartate kinase by the levels of both L-threonine and L-lysine; and second through the control of the level of dihydrodipicolinate synthase. Increased production of L-lysine may be therefore obtained in Corynebacteria by deregulating and increasing the activity of these two enzymes.

In addition to the biochemical pathway leading to L-lysine synthesis, recent evidence indicates that the transportation of L-lysine out of cells into the media is another factor to be considered in the development of lysine overproducing strains of *C. glutamicum*. Studies by Krämer and colleagues indicate that passive transport of lysine out of the cell, as the result of a leaky membrane, is not the sole explanation for lysine efflux; their data suggest a specific carrier with the following properties: (1) the transporter possesses a rather high Km value for lysine (20 mM); (2) the transporter is an $OH^-$ symport system (uptake systems are $H^+$ antiport systems); and (3) the transporter is positively charged, and membrane potential stimulates secretion (S. Bröer and R. Kräer, *Eur. J. Biochem.* 202: 137–143 (1991).

Several fermentation processes utilizing various strains isolated for auxotrophic or resistance properties are known in the art for the production of L-lysine: U.S. Pat. No. 2,979,439 discloses mutants requiring homoserine (or methionine and threonine); U.S. Pat. No. 3,700,557 discloses mutants having a nutritional requirement for threonine, methionine, arginine, histidine, leucine, isoleucine, phenylalanine, cystine, or cysteine; U.S. Pat. No. 3,707,441 discloses a mutant having a resistance to a lysine analog; U.S. Pat. No. 3,687,810 discloses a mutant having both an ability to produce L-lysine and a resistance to bacitracin, penicillin G or polymyxin; U.S. Pat. No. 3,708,395 discloses mutants having a nutritional requirement for homoserine, threonine, threonine and methionine, leucine, isoleucine or mixtures thereof and a resistance to lysine, threonine, isoleucine or analogs thereof; U.S. Pat. No. 3,825,472 discloses a mutant having a resistance to a lysine analog; U.S. Pat. No. 4,169,763 discloses a mutant strains of *Corynebacterium* that produce L-lysine and are resistant to at least one of aspartic analogs and sulfa drugs; U.S. Pat. No. 5,846,790 discloses a mutant strain able to produce L-glutamic acid and L-lysine in the absence of any biotin action-surpressing agent; and U.S. Pat. No. 5,650,304 discloses a strain belonging to the genus *Corynebacterium* or *Brevibacterium* for the production of L-lysine that is resistant to 4-N-(D-alanyl)-2, 4-diamino-2,4-dideoxy-L-arabinose 2,4-dideoxy-L-arabinose or a derivative thereof.

More recent developments in the area of L-lysine fermentive production in Corynebacteria involve the use of molecular biology techniques to augment lysine production. The following examples are provided as being exemplary of the art: U.S. Pat. Nos. 4,560,654 and 5,236,831 disclose an L-lysine producing mutant strain obtained by transforming a host *Corynebacterium* or *Brevibacterium* microorganism which is sensitive to S-(2-aminoethyl)-cysteine with a recombinant DNA molecule wherein a DNA fragment conferring resistance to S-(2-aminoethyl)-cysteine and lysine producing ability is inserted into a vector DNA; U.S. Pat. No. 5,766,925 discloses a mutant strain produced by integrating a gene coding for aspartokinase, originating from Coryneform bacteria, with desensitized feedback inhibition by L-lysine and L-threonine, into chromosomal DNA of a Coryneform bacterium harboring leaky type homoserine dehydrogenase or a Coryneform bacterium deficient in homoserine dehydrogenase gene.

Many process designed utilizing bacterial mutant strains are designed to weaken bacterial growth and hence to enhance the yield of amino acid production through supplementation with other nutrients. Usually, mutants designed to improve the percent yield of an amino acid from substrates such as glucose will also lose their ability for vigorous growth like their wild type strains. Besides resulting in an overall decrease in amino acid yield, these mutants also require more nutrients to support their growth, which can increase the cost in the production significantly.

Thus, there is a continuing need in the art for the development of novel amino acid producing bacterial strains that enable maximized yields of a particular amino acid at a low cost of production. In view of these problems, an alternative method comprises special mutants and media that is employed to increase the productivity and to decrease the ingredient cost.

SUMMARY OF THE INVENTION

The invention provides generally for novel microorganisms with improved raffinate resistance and improved growth properties, which enables higher yields of amino acid to be produced.

A first object of the invention provides novel methods for the production of microorganisms with increased ability to produce amino acids. In a first embodiment of the invention, a method is provided for the production of a novel strain by way of mutagenesis of an amino acid-producing, parental bacterial strain and subsequent selection for the improved raffinate resistant strains of the invention. In a more specific embodiment of the invention, the methods are drawn to amino acid-producing, parental bacterial strains such as *Corynebacterium* and *Brevibacterium*. A particularly favored embodiment is drawn to a method for the production of an improved raffinate-resistant, amino acid producing bacterial strain that is *Brevibacterium* which produces L-lysine.

Another object of the invention is drawn to novel bacterial strains with improved raffinate-resistance, improved growth characteristics and that produce larger amounts of amino acid. In a first embodiment, bacterial strains of the invention are produced by a process wherein a parental bacterial strain is subjected to mutagenesis and mutant progeny bacteria are selected for improved raffinate-resistance, improved growth characteristics and improved amino acid production. A more specific embodiment is drawn to novel *Corynebacterium* or *Brevibacterium* microorganisms with improved raffinate-resistance, improved growth characteristics and improved amino acid production. Particularly favored embodiments of the invention are drawn to *Brevibacterium* that produce large amounts of L-lysine. Most favored embodiments are drawn to the strains ADM L63.148 (NRRL B-30059), ADM L64.132 (NRRL B-30060), ADM L69.53 (NRRL B-30061), ADM L69.74 (NRRL B-30062), and ADM L69.100 (NRRL B-30063), or mutants thereof.

A third object of the invention provides processes for the production of an amino acid comprising the steps of (a) culturing a bacterium in a raffinate containing medium and (b) recovering the amino acid from the culture media. In a preferred embodiment, the cultured bacteria of step (a) is obtained by a method in which an amino acid-producing, parental bacterial strain is subjected to mutagenesis and progeny are selected for improved raffinate-resistance, improved growth characteristics and improved production of an amino acid. Favored embodiments are drawn to processes for the production of an amino acid that utilize *Corynebacterium* or *Brevibacterium*. Particularly favored embodiments of the invention for processes for the production of an amino acid utilize *Brevibacterium* that produce L-lysine.

It is to be understood that both the foregoing general description and the following detailed description are exemplary and explanatory only and are intended to provide further explanation of the invention as claimed.

DETAILED DESCRIPTION OF THE PREFERRED EMBODIMENTS

1. Definitions

Figure 1A:
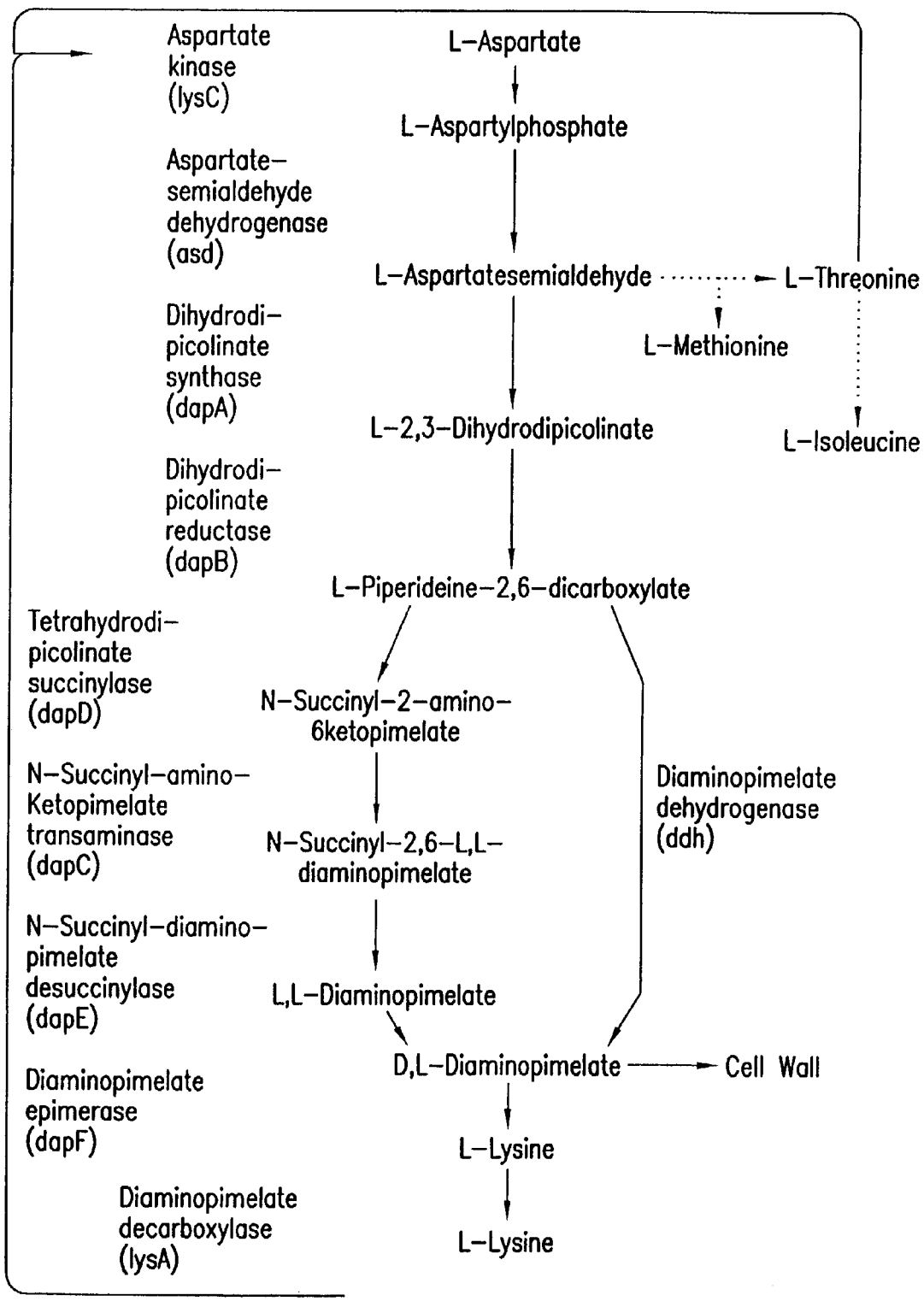
FIG. 1. A) A schematic presentation of the biochemical pathway leading to L-lysine production in *Corynebacterium*; B) A schematic presentation of the biochemical pathway leading to L-isoleucine production in *Corynebacterium*.
Figure 1B:
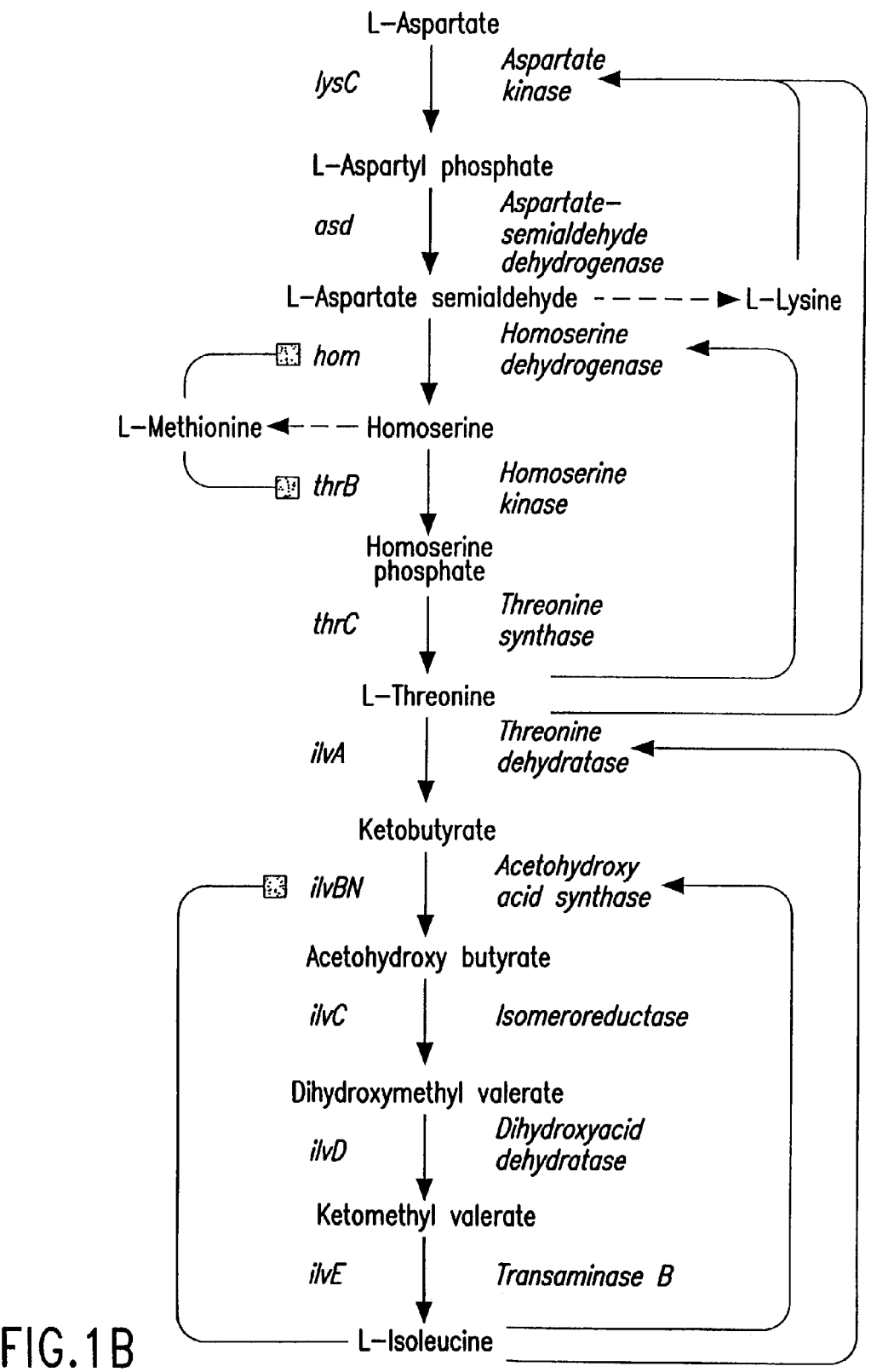

In order to provide a clear and consistent understanding of the specification and claims, including the scope to be given such terms, the following definitions are provided.

High Yield Derivative: As used herein, the term refers to strain of microorganism that produces a higher yield from dextrose of a specific amino acid when compared with the parental strain from which it is derived.

Mutation: As used herein, the term refers to a single base pair change, insertion or deletion in the nucleotide sequence of interest.

Operon: As used herein, the term refers to a unit of bacterial gene expression and regulation, including the structural genes and regulatory elements in DNA.

Parental Strain: As used herein, the term refers to a strain of microorganism subjected to some form of mutagenesis to yield the microorganism of the invention.

Phenotype: As used herein, the term refers to observable physical characteristics dependent upon the genetic constitution of a microorganism.

Raffinate: As used herein, the term refers to a wastestream product from an ion-exchange operation for lysine recovery. Raffinate contains a large amount of ammonia sulfate, L-lysine, other amino acids, salts, and carbohydrates such as isomaltose. Sterilization of a raffinate-containing medium using heat treatment produces amino acid derivatives and other metabolic antagonists which cause the inhibition of culture growth.

Heat sterilized raffinate-containing medium may be used to select microorganisms, e.g., *Brevibacterium* or *Corynebacterium*, that are resistant to amino acid derivatives contained therein that inhibit culture growth; that are resistant to metabolic inhibitors contained therein that inhibit culture growth and/or that are resistant to degradation products of lysine and/or precursors to lysine contained therein that inhibit culture growth.

Relative Growth: As used herein, the term refers to a measurement providing an assessment of growth by directly comparing growth of a parental strain with that of a progeny strain over a defined time period and with a defined medium.

Mutagenesis: As used herein, the term refers to a process whereby a mutation is generated in DNA. With "random" mutatgenesis, the exact site of mutation is not predictable, occurring anywhere in the chromosome of the microorganism, and the mutation is brought about as a result of physical damage caused by agents such as radiation or chemical treatment.

2. Mutagenesis of Parental Bacterial Strains

The invention provides methods for the production of microorganisms that produce large amounts of an amino acid and have improved resistance to raffinate. Through the course of studies, it has now been found that ammonia sulfate which is required for the growth and amino acid biosynthesis may be replaced with raffinate, a wastestream product from an ion-exchange operation of lysine recovery. Raffinate contains a lot of ammonia sulfate, L-lysine, other amino acids, salts, and carbohydrates such as isomaltose. During heat treatment to sterilize the medium, however, this raffinate medium produces a lot of amino acid derivatives and other metabolic antagonists which causes the inhibition of growth for culture. To overcome this problem, a method was designed to select strains which can resist high levels of raffinate in the medium and increase their amino acid production.

Bacterial strains of the invention are preferably made by means of mutagenesis of a parental bacterial strain followed by selection of the improved raffinate-resistant phenotype. Parental microorganisms may be selected from any organism known in the art to be useful for the fermentative production of amino acids; favored parental microorganisms are *Corynebacterium* and *Brevibacterium* that produce an amino acid, and most particularly favored organisms are *Corynebacterium* and *Brevibacterium* that produce L-lysine.

In a first embodiment, the invention provides a methods for the production of improved raffinate-resistant, amino acid-producing, bacterial strains comprising:
(a) subjecting a parental bacterial strain A to mutagenesis;
(b) contacting said mutagenized parental strain A with a medium containing at least about 1% raffinate based on ammonia sulfate content;
(c) selecting raffinate-resistant bacterial strain B; and
(d) determining L-lysine production of said raffinate-resistant bacterial strain B.

The parental strain may be mutagenized using any random mutagenesis technique known in the art, including, but not limited to, radiation and chemical procedures. Particularly preferred is random chemical mutagenesis, and most preferable is mutagenesis using a suitable agent such as N-methyl-N'-nitro-N-nitrosoguanidine (NTG).

General methods for mutagenesis and selection of novel bacterial strains are well known in the art and are described, for example, in J. H. Miller, *Experiments in Molecular Genetics*, Cold Spring Harbor Laboratory Press, Cold Spring Harbor, N.Y. (1972); J. H. Miller, *A Short Course in Bacterial Genetics*, Cold Spring Harbor Laboratory Press, Cold Spring Harbor, N.Y. (1992); M. Singer and P. Berg, *Genes & Genomes*, University Science Books, Mill Valley, Calif. (1991); J. Sambrook, E. F. Fritsch and T. Maniatis, *Molecular Cloning: A Laboratory Manual,* 2d ed., Cold Spring Harbor Laboratory Press, Cold Spring Harbor, N.Y. (1989); P. B. Kaufman et al., *Handbook of Molecular and Cellular Methods in Biology and Medicine*, CRC Press, Boca Raton, Fla. (1995); *Methods in Plant Molecular Biology and Biotechnology*, B. R. Glick and J. E. Thompson, eds., CRC Press, Boca Raton, Fla. (1993); and P. F. Smith-Keary, *Molecular Genetics of Escherichia coli*, The Guilford Press, New York, N.Y. (1989).

Strains of the invention have an improved raffinate resistant phenotype, which is determined by the concentration of raffinate, as measured by ammonium sulfate content, in the selection medium employed. In a first embodiment, phenotype selection may be done in a medium containing at least about 1% raffinate. In a most preferred embodiment, microorganisms of the invention are selected in medium containing about 5% raffinate. Other examples include at least about 2%, 3%, 4%, 5%, 6%, 7%, and 8% raffinate containing medium for use in the selection of improved raffinate resistant strains.

The invention provides generally for novel microorganisms with improved raffinate resistance and improved growth properties, which enables higher yields of amino acid to be produced. An important element or property of the methods, processes or microorganisms of the invention is related to raffinate resistance.

Skilled artisans in the art of fermentative amino acid production are familiar with the term "raffinate" as used herein. However, for the purposes of more fully providing a detailed description of Applicants' invention, a definition of raffinate and a method for its production are provided.

The term "raffinate" is most closely associated with the chemical engineering field in the area of liquid-liquid extraction. The term is defined in solvent refining as "that portion of the treated liquid mixture that remains undissolved and is not removed by the selective solvent" (Dictionary of Scientific and Technical Terms, Sybil P. Parker, ed., McGraw-Hill (1989)). As used herein, the term is associated with the application of ion-exchange chromatography in the isolation of amino acids. In an analogous fashion to the process of liquid-liquid extraction, the term raffinate as used in connection with ion-exhange chromatography refers to that portion of the liquid mixture that is not selectively bound by the chromatographic resin. More specifically, in connection with the fermentative production of amino acids, the raffinate is that portion of the cell culture media that does not bind to the chromatographic column; raffinate is the broth effluent waste stream product generated during the ion-exchange chromatographic purification of an amino acid. Typically, as used herein, raffinate refers to the first waste stream product generated after the initial application of the growth media to the ion-exchange resin.

A variety of ion-exchange chromatographic methods may be utilized for the purification of amino acids. Typically, cation exchange resins are utilized for the purification of lysine. Ion-exchange chromatography may be done utilizing a fixed bed or simulated moving bed resin. For example, Van Walsem and Thompson describe a simulated moving bed technique for the isolation of lysine (Van Walsem, H. J. and Thompson, M. C., *J. Biotechnology* 59:127–132 (1997); U.S. Pat. Nos. 4,714,767 and 5,684,190 describe the use of a fixed bed chromatographic technique for the purification of amino acids and Wolfgang and Prior utilize an annular chromatograph to achieve a continuous mode of operation in the separation of carbohydrates (Wolfgang, J. and Prior, A., *Separation Science and Technology* 32:71–82 (1997)). Thus, the specific chromatographic method of generating raffinate may vary, but the underlying principle defining raffinate remains constant.

For exemplary purposes only, Applicants provide in Example 5 details for the production of raffinate for use as a cell growth medium supplement. As one skilled in the art would know, raffinate may be qualitatively characterized according to the specific amino acid produced in the fermentation medium from which the raffinate is isolated; for example, raffinate may be known as lysine-raffinate when isolated from lysine fermentation medium, glycine-raffinate when isolated from glycine fermentation medium, isoleucine-raffinate when isolated from isoleucine fermentation medium, etc. It will be readily apparent to those skilled in the art that when the general term raffinate is used herein, the specific type of raffinate selected will depend upon practitioner design.

The example provided herein is exemplary for the production of raffinate, in particular for lysine-raffinate. As will be obvious to those skilled in the art, other methods may be utilized in the generation of raffinate.

3. Improved Raffinate Resistant Strains of the Invention

Another object of the invention is drawn to microorganisms that have improved raffinate resistance and that produce an amino acid. As one skilled in the art will know, such microorganisms may selected to have improved resistance to any specific type of raffinate, for example, glycine-raffinate, valine-raffinate, isoleucine-raffinate, lysine-raffinate, etc. In a particularly preferred embodiment, the microorganisms have improved resistance to lysine-raffinate.

In a specific embodiment of the invention, the raffinate-resistant microorganisms are produced by a process wherein:
  (a) a parental bacterial strain A is subjected to mutagenesis;
  (b) the mutagenized parental strain A is contacted with a medium containing at least about 1% raffinate based on ammonia sulfate content;
  (c) a raffinate-resistant bacterial strain B is selected; and
  (d) amino acid production of said raffinate-resistant bacterial strain B is determined.

Selection of parental bacterial strains, mutagenesis and the selection of microorganisms of the invention with improved raffinate resistance may be done as heretofore described.

A more specific embodiment of the invention is drawn to *Corynebacterium* or *Brevibacterium*; especially favored are *Corynebacterium* or *Brevibacterium* that produce L-lysine.

The invention also provides a *Corynebacterium* strain producing at least about 10 g L-lysine/liter/in 24 hours when grown in a medium containing at least about 1% raffinate.

A particularly favored embodiment of the invention is drawn to an L-lysine producing *Corynebacterium* strain, wherein said strain is selected from the group consisting of NRRL B-30059, NRRL B-30060, NRRL B-30061, NRRL B-30062, NRRL B-30063 and mutants thereof.

4. Amino Acid Production and Purification

Other embodiments of the invention are drawn to processes for the production of an amino acid in a raffinate-containing medium. Such processes involve (a) the culturing of an improved raffinate resistant bacterial strain and (b) recovery of the amino acid from culture media.

In a first specific embodiment, the invention provides a process for the production of an amino acid comprising:
  (a) culturing a bacterial B strain in a medium containing raffinate, whereby said strain is obtained by the following method:
    (i) selecting a parental bacterial strain A that produces an amino acid;
    (ii) subjecting said parental strain A to mutagenesis;
    (iii) selecting an improved raffinate-resistant bacterial strain B; and
  (b) recovering the amino acid from the culture media.

Selection of parental bacterial strains, mutagenesis and the selection of microorganisms of the invention with improved raffinate resistance may be done as heretofore described.

In preferred embodiments of the invention, other processes are drawn to parental strains selected from the group consisting of L-lysine producing *Corynebacterium* and *Brevibacterium* microorganisms, and a most preferred embodiment of the invention is drawn to a parental strain that is *Brevibacterium* that produces the amino acid L-lysine.

The processes of the invention may further vary by way of the specific method of culturing the microorganisms of the invention. Thus, a variety of fermentation techniques are known in the art which may be employed in processes of the invention drawn to the production of amino acids.

Illustrative examples of suitable carbon sources include, but are not limited to: carbohydrates, such as glucose, fructose, sucrose, starch hydrolysate, cellulose hydrolysate and molasses; organic acids, such as acetic acid, propionic acid, formic acid, malic acid, citric acid, and fumaric acid; and alcohols, such as glycerol.

Illustrative examples of suitable nitrogen sources include, but are not limited to: ammonia, including ammonia gas and aqueous ammonia; ammonium salts of inorganic or organic acids, such as ammonium chloride, ammonium phosphate, ammonium sulfate and ammonium acetate; and other nitrogen-containing, including meat extract, peptone, corn steep liquor, casein hydrolysate, soybean cake hydrolysate and yeast extract.

Generally, amino acids may be commercially produced from the invention in fermentation processes such as the batch type or of the fed-batch type. In batch type fermentations, all nutrients are added at the beginning of the fermentation. In fed-batch or extended fed-batch type fermentations one or a number of nutrients are continuously supplied to the culture, right from the beginning of the fermentation or after the culture has reached a certain age, or when the nutrient(s) which are fed were exhausted from the culture fluid. A variant of the extended batch of fed-batch type fermentation is the repeated fed-batch or fill-and-draw fermentation, where part of the contents of the fermenter is removed at some time, for instance when the fermenter is full, while feeding of a nutrient is continued. In this way a fermentation can be extended for a longer time.

Another type of fermentation, the continuous fermentation or chemostat culture, uses continuous feeding of a complete medium, while culture fluid is continuously or semi-continuously withdrawn in such a way that the volume of the broth in the fermenter remains approximately constant. A continuous fermentation can in principle be maintained for an infinite time.

In a batch fermentation an organism grows until one of the essential nutrients in the medium becomes exhausted, or until fermentation conditions become unfavorable (e.g., the pH decreases to a value inhibitory for microbial growth). In fed-batch fermentations measures are normally taken to maintain favorable growth conditions, e.g., by using pH control, and exhaustion of one or more essential nutrients is prevented by feeding these nutrient(s) to the culture. The microorganism will continue to grow, at a growth rate dictated by the rate of nutrient feed. Generally a single nutrient, very often the carbon source, will become limiting for growth. The same principle applies for a continuous fermentation, usually one nutrient in the medium feed is limiting, all other nutrients are in excess. The limiting nutrient will be present in the culture fluid at a very low concentration, often unmeasurably low. Different types of nutrient limitation can be employed. Carbon source limitation is most often used. Other examples are limitation by the nitrogen source, limitation by oxygen, limitation by a specific nutrient such as a vitamin or an amino acid (in case the microorganism is auxotrophic for such a compound), limitation by sulphur and limitation by phosphorous.

Methods for the recovery and purification of amino acids, particularly L-lysine, are well known to those skilled in the art. Typically, an amino acid may be recovered from the growth medium by cation exchange, after centrifugation and filtration to remove cells. U.S. Pat. No. 5,684,190 describes the recovery of an amino acid such as L-lysine that involves (1) passage of the amino acid containing aqueous solution over a primary cation exchange resin to absorb the amino acid onto the resin at a pH lower than its isoelectric point, subsequently followed by elution of the amino acid by increasing the pH with ammonium hydroxide to produce a first solution; and (2) passage of the first solution over a secondary cation exchange resin in a similar fashion to further eliminate impurities.

Another example may be provided by U.S. Pat. No. 4,714,767, which provides a process for separating basic amino acids from an aqueous solution using cation exchange resin towers in series. The process comprises repetitive adsorption and elution steps in sequence, wherein the washing water employed in the absorption and elution steps is obtained by recycling the latter portion of a liquid discharged from a first tower absorption step or elution step in a subsequent cycle.

Eluants obtained from such cation exchange isolation procedures may be concentrated by evaporation, which additionally provides for the elimination of ammonia. The amino acid may then be crystallized from solution with hydrochloric acid, producing for example L-lysine.HCl.2H$_2$O. After centrifugation or filtration, the isolated L-lysine crystals are dried.

EXAMPLES

Example 1

Mutagenesis, Screening And Selection for Improved Raffinate Resistant Microorganisnis The lysine producing strains such a T125, L58.23, and 96T116, whose growth is inhibited by higher concentrations of raffinate, were subjected to mutagenesis, and mutants showing resistance to higher concentrations of raffinate were recovered. For mutagenesis, bacterial cultures were grown to mid-log phase in medium B (Table 1), pelleted by centrifugation and resuspended in 2 mL of filter-steriled TM buffer in a 15 ml polypropylene conical tube (Tris.HCL 6.0 g/L, maleic acid 5.8 g/L, (NH$_4$)2SO$_4$1.0 g/L, Ca(NO$_3$)$_2$ 5 mg/L, MgSO$_4$.7H$_2$O 0.1 g/L FeSO$_4$.7H$_2$O 0.25 mg/L, adjusted to pH 6.0 using KOH). The 2 mL cell suspension was mixed with 50 µL of a 5.0 mg/L solution of N'-nitro-N-nitrosoguanidine (NTG), then incubated at 30° C. for 30 minutes. An untreated cell suspension was similarly incubated as a control for estimating the kill rate. After incubation, 10 mL of TM buffer was added to each tube, and the cells were pelleted by centrifugation, washed twice in TM buffer, and resuspended in 4.0 mL of 0.1 M NaH$_2$PO$_4$ (phosphate buffer) adjusted to pH 7.2 using KOH. The washed cell suspensions were further diluted in phosphate buffer, and aliquots were spread on plates of medium A (Table 1). After incubation at 30° C. for 4–6 days, colonies growing on medium A agar were picked and tested for improved potential to produce L-lysine from dextrose in shaker flasks and fermentors.

Example 2

The Growth of Strains in Raffinate Media

For each tested strain (Table 2), 0.1 mL of frozen culture was inoculated into a 250 mL baffled flask containing 20 mL raffinate medium C (Table 1), then incubated for 18 hours at 30° C., at 240 rpm. After incubation, 50 µl of culture was removed and diluted to a ratio of 1:100 in 0.1 N HCl solution. The optical density (OD) of the diluted sample was measured at 660 nm with a spectrophotometer. The results are shown in Table 2. All strains with improved raffinate resistance (RF), L63.148, L64.132, L69.53, and L69.74, grew better (higher OD) than their parental strains, 108T125, LS8.23, and 96T116, in the raffinate medium C.

Example 3

Dextrose Consumption, Growth, and Lysine Production in Shaker Flask Fermentation For each strain, 0.1 mL of a frozen culture was inoculated into a 250 mL baffled flask containing 20 mL of seed medium C and incubated for 18 hours at 30° C., 240 rpm. Two mL of seed culture were used to inoculated 20 mL of fermentation medium D in a 250 mL baffled flask. The flasks were then shaken for 24 hours at 30° C. and 240 rpm. After 24 hours of fermentation, samples were removed for analysis. To measure dextrose concentrations, 100 µL of sample were removed and diluted 1:50 with deionized (DI) water and measured with a YSI biochemistry analyzer (Yellow Springs Instrument Co. Inc.). L-lysine concentrations were determined by HPLC. Optical density measurements were taken to measure growth as described in Example 2. Results are presented in Table 3; all raffinate resistant strains, L63.148, L64.132, L69.53 and L69.74, grew better, used dextrose more efficiently, and produced more L-lysine than their parent strains, 108T125, L58.23, and 96T116.

Example 4

Growth and L-Lysine Production in Bench Scale Fermentors

Bench scale fermentations were set up using a two stage inoculum protocol. The first stage media was composed of 50.0 g/l sucrose, 3.0 g/l K$_2$HPO$_4$, 3.0 g/l urea, 0.5 g/l MgSO$_4$-7H$_2$O, 30.0 g/l soy peptone, 5.0 g/l yeast extract, 0.765 mg/l biotin, 3.0 mg/l thiamine HCl, and 0.125 g/l niacinamide. A 2 liter baffled shake flask containing 500 mls of this media was inoculated with the culture and incubated at 30° C. and 250 rpm for 19 hrs. At this point, 22.5 mls of the mature first culture was used to inoculate the second stage inoculum media.

The second stage inoculum was prepared with 3000 mls of medium in a 6.6 liter fermentor. The medium formulation was 20.0 g/l (db) corn steep liquor, 10.0 g/l ammonium sulfate as raffinate, 12.0 mg/l MnSO$_4$—H$_2$O, 3.0 g/l biotin, 3.0 g/l thiamine HCl, 125 mg/l niacinamide, 0.5 mls 1 antifoam, and 60 g/l dextrose, sterilized separately as a 360 g/l solution and added to the fermentorjust prior to inoculation. The fermentor was operated at 32° C., 1.2 vvm air, 600 rpm, and a pH control point of 7.2. pH control was accomplished by the addition of NH$_3$ or NH$_4$OH. After 18–20 hrs the inoculum was considered mature and used to inoculate the production stage vessel.

Production stage medium was composed of 40 g/l (db) corn steep liquor, 20 g/l ammonium sulfate as raffinate, 12.0 mg/l MnSO$_4$—H$_2$O, 0.75 mls/l antifoam and 12 g/l dextrose, sterilized separately as a 250 g/l solution and added just prior to inoculation. Media formulation was based on a 2.1 liter initial volume which includes 500 mls of mature second stage broth as inoculum. Operating parameters were the following: 32° C., 2.1 vvm air, and an initial and control point pH of 7.2. pH control was again done with NH$_3$ or NH$_4$OH. Agitation was initially 600 rpm, increased to 700 rpm at 9 hrs culture time and 900 rpm at 19 hrs culture time.

The fermentation was fed on demand, as indicated by pH increases due to dextrose depletion, a mixture of dextrose and ammonium sulfate. The feed was prepared by sterilizing separately 2310 g dextrose +800 mls water and a volume of raffinate containing a total of 176 g of ammonium sulfate, then combining the two solutions upon cooling to ambient temperature. Total fermentation time was 48 hrs. The vessel size was the same as that used for the second stage inoculum development.

Results of an experiment comparing the parent strain to the above described isolates in bench scale fermentation are presented in Table 4.

Example 5

Production of Raffinate

As previously described, raffinate may be qualitatively characterized according to the specific amino acid produced in the fermentation medium from which the raffinate is isolated. The example provided herein is for the production of lysine-raffinate. However, one skilled in the art would know, other types of raffinate, e.g., valine- or isoleucine-raffinate, etc., may be similarly produced by simply starting with the appropriate fermentation broth, e.g., valine or isoleucine fermentation broth, etc.

As a first step in the production of lysine-raffinate, lysine fermentation broth is diluted to a lysine concentration of 65.5 g/l. After ultrafiltration to generate a permeate with a lysine concentration of 40.3 g/l, the permeate is then concentrated to 123 g/l lysine with a total dry solids concentration of 207 g/l.

The permeate concentrate is then fed into a chromatographic separation system, for example I-SEP or C-SEP produced by Advanced Separation Technologies Incorporated (St. Petersburg, Fla.). Ion exchange chromatographic separation systems are commonly known in the art, as exemplified by U.S. Pat. Nos. 4,808,317 and 4,764,276, which are incorporated herein by reference. The waste effluent obtained therefrom is considered the "dilute lysine-raffinate" solution. The dilute lysine-raffinate solution has a pH of 5.1 and it contains 34.3 g/l ammonium sulfate and 2.8 g/l lysine with a total solids level 67 g/l.

The dilute lysine-raffinate solution is concentrated to 295 g/l total solids. Quantitated components of this "concentrated lysine-raffinate" solution include the following: 137.9 g/l ammonium sulfate, 14.8 g/l lysine, 8.7 g/l valine, 8.1 g/l alanine, 2.4 g/l lactic acid and 2.2 g/l acetic acid. This concentrated lysine-raffinate solution is used in media preparation.

TABLES

The following tables are referenced in the Examples section.

TABLE 1

Media Employed in Examples 1, 2, and 3

| Ingredients (amount/L) | A | B | C | D |
|---|---|---|---|---|
| Glucose | 20 g | | 30 g | 68 g |
| Sucrose | | 50 g | | |
| L-Alanine | 0.5 g | 0.5 g | | |
| L-Methionine | 0.5 g | 0.5 g | | |
| L-Threonine | 0.25 g | 0.25 g | | |
| Biotin | 0.05 mg | 0.756 mg | 0.003 g | 0.405 mg |
| Thiamine | 0.2 mg | 0.003 g | 0.003 g | |
| Niacinamide | 0.05 g | 0.125 g | 0.125 g | |
| Polypeptone Peptone (BBL) | | 20 g | | |
| Beef Extract (BBL) | | 5 g | | |
| Corn Steep Liquor[1] | | | 20 g | |
| Raffinate[2] | 60 g | | 10 g | 40 g |
| Urea | 2.5 g | 3 g | | 50 g |
| Amonia Sulfate | 10 g | | | |
| $K_2HPO_4$ | | 3 g | | |
| $KH_2PO_4$ | 1 g | | | |
| $MgSO_4 \cdot 7H_2O$ | 0.4 g | 0.5 g | | |
| $MnSO_4 \cdot H_2O$ | 0.01 g | | 0.01 g | 0.01 g |
| NaCl | 1 g | | | |
| $FeSO_4 \cdot 7H_2O$ | 0.01 g | | | |
| $CaCO_3$ | | | 50 g | 50 g |
| Agar | 15 g | | | |
| pH (before autoclave) | 7.2 | 7.3 | 7.4 | 7.4 |

[1]The amount of corn steep liquor is expressed as grams of dried solids per liter of medium.
[2]The amount of raffinate is expressed as grams of ammonia sulfate per liter of medium.

TABLE 2

The Growth of Strains in Medium C Containing Raffinate

| Strain | 108T125 | L63.148 | L58.23 | L64.132 | 96T116 | L69.53 | L69.74 |
|---|---|---|---|---|---|---|---|
| Type | Wild[1] | RF[2] | Wild | RF | Wild | RF | RF |
| $OD_{660}$ | 15.9 | 27.4 | 27.1 | 34.5 | 22.2 | 31.6 | 30.3 |

[1]Strains 108T125, L58.23, and 96T116 are parent and wild type strains used to generate the improved raffinate resistant strains of the invention.
[2]Strains L63.148, L64.132, L69.53, and L69.74 are improved raffinate resistant (RF) strains derived from their wild type parental strains as described.

TABLE 3

The Dextrose Consumption (Dex), Growth ($OD_{660}$), and Lysine Production (Lys) of Strains in 24 hr Shaker Flask Fermentation in Medium D

| Strain | 108T125 | L63.148 | L58.23 | L64.132 | 96T116 | L69.53 | L69.74 |
|---|---|---|---|---|---|---|---|
| Type | Wild | RF | Wild | RF | Wild | RF | RF |

TABLE 3-continued

The Dextrose Consumption (Dex), Growth (OD$_{660}$), and Lysine
Production (Lys) of Strains in 24 hr Shaker Flask Fermentation in
Medium D

| Dex, g/L | 25.9 | 66.7 | 40.6 | 68.8 | 45.8 | 78.8 | 76.6 |
|---|---|---|---|---|---|---|---|
| OD$_{660}$ | 20.5 | 43.2 | 26.3 | 47.9 | 30.5 | 47.4 | 42.8 |
| Lys, g/L | 9.4 | 18.8 | 14.1 | 23.3 | 15.5 | 24.6 | 23.2 |

TABLE 4

Parent and Progeny Comparison of Growth (OD660)
and L-lysine Production in 6.6 l fermentors

| Strain | | OD @ 660 nm | Total Product[1] | g lysine/l/hr[2] |
|---|---|---|---|---|
| 96T116 | Wild | 83.8 | 583 g | 5.78 |
| L69.53 | RF | 112.5 | 776 g | 7.70 |
| L69.74 | RF | 122.4 | 807 g | 8.01 |
| L69.100 | RF | 93.3 | 745 g | 7.48 |

[1]Total Product denotes total grams of lysine in the fermentor at harvest.
[2]Calculation based on the initial 2.1 liter volume.

What is claimed is:

1. A process for the production of L-lysine comprising culturing a raffinate-resistant bacterial strain B in a bacterial fermentation medium containing at least about 2% raffinate based on ammonium sulfate content, wherein said raffinate is the broth effluent waste stream product generated during the ion-exchange chromatographic purification of L-lysine, wherein said raffinate-resistant bacterial strain B is obtained by:
   (i) selecting a parental bacterial strain A that produces L-lysine;
   (ii) subjecting said parental bacterial strain A to mutagenesis;
   (iii) culturing the mutagenized parental bacterial strain A in a bacterial selection medium containing at least about 1% raffinate based on ammonium sulfate content, wherein said raffinate is the broth effluent waste stream product generated during the ion-exchange chromatographic purification of L-lysine;
   (iv) selecting said raffinate-resistant bacterial strain B from the bacterial selection medium containing said mutagenized parental bacterial strain A of part (iii), wherein said raffinate-resistant bacterial strain B is able to grow to a higher optical density at a wavelength of 660 nm than said parental bacterial strain A;
   (v) culturing said raffinate-resistant bacterial strain B in a bacterial fermentation medium containing at least about 2% raffinate based on ammonium sulfate content, wherein said raffinate is the broth effluent waste stream product generated during the ion-exchange chromatographic purification of L-lysine, wherein said bacterial strain B produces a higher amount of L-lysine compared to said parental bacterial strain A; and
   (vi) recovering the L-lysine from said bacterial fermentation medium.

2. The process of claim 1, wherein the bacterial fermentation medium contains at least 4% raffinate based on animonium sulfate content, wherein said raffinate is the broth effluent waste stream product generated during the ion-exchange chromatographic purification of L-lysine.

3. The process of claim 1, wherein the amount of L-lysine produced is at least about 10 grams of L-lysine per liter of said fermentation medium in 24 hours.

4. The process of claim 2, wherein the amount of L-lysine produced is at least about 10 grams of L-lysine per liter of said fermentation medium in 24 hours.

5. The process of claim 1, wherein said parental bacterial strain A and said raffinate-resistant bacterial strain B is a *Corynebacterium* sp.

6. The process of claim 5, wherein said raffinate-resistant bacterial strain B is a *Corynebacterium* strain selected from the group consisting of NRRL B-20059, NRRL B-30060, NRRL-30061, NRRL B-30062, and NRRL B 30063.

* * * * *